(12) United States Patent
Schultz et al.

(10) Patent No.: US 10,729,669 B2
(45) Date of Patent: Aug. 4, 2020

(54) COMPOSITIONS AND METHODS FOR TREATING CANCER

(71) Applicant: UNIVERSITY OF IOWA RESEARCH FOUNDATION, Iowa City, IA (US)

(72) Inventors: Michael K. Schultz, Iowa City, IA (US); Somya Kapoor, Iowa City, IA (US); Andrean L. Simons-Burnett, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/748,506

(22) PCT Filed: Jul. 26, 2016

(86) PCT No.: PCT/US2016/043993
§ 371 (c)(1),
(2) Date: Jan. 29, 2018

(87) PCT Pub. No.: WO2017/019664
PCT Pub. Date: Feb. 2, 2017

(65) Prior Publication Data
US 2018/0214402 A1 Aug. 2, 2018

Related U.S. Application Data

(60) Provisional application No. 62/198,001, filed on Jul. 28, 2015, provisional application No. 62/241,379, filed on Oct. 14, 2015.

(51) Int. Cl.
| | | |
|---|---|---|
| *A61K 31/192* | (2006.01) | |
| *A61K 31/437* | (2006.01) | |
| *A61K 31/4706* | (2006.01) | |
| *A61K 31/662* | (2006.01) | |
| *A61P 35/00* | (2006.01) | |
| *A61K 31/66* | (2006.01) | |
| *A61K 39/395* | (2006.01) | |
| *C07K 16/28* | (2006.01) | |

(52) U.S. Cl.
CPC .......... *A61K 31/192* (2013.01); *A61K 31/437* (2013.01); *A61K 31/4706* (2013.01); *A61K 31/66* (2013.01); *A61K 31/662* (2013.01); *A61K 39/3955* (2013.01); *A61P 35/00* (2018.01); *C07K 16/2818* (2013.01); *C07K 2317/21* (2013.01)

(58) Field of Classification Search
CPC ............... A61K 31/192; A61K 31/437; A61K 31/4706; A61K 31/662; A61K 31/66; A61K 39/3955; A61P 35/00; C07K 16/2818; C07K 2317/21
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 6,338,834 B1 | 1/2002 | Jurisson et al. |
| 6,607,709 B1 | 8/2003 | Jurisson et al. |
| 6,680,045 B2 | 1/2004 | Jurisson et al. |
| 7,321,027 B2 | 1/2008 | Mahmood et al. |
| 7,915,245 B2 * | 3/2011 | Srivastava ............. A61K 31/41 514/183 |
| 8,143,271 B2 * | 3/2012 | Ibrahim .................. C07C 37/62 514/300 |
| 9,801,922 B2 | 10/2017 | Spitz et al. |
| 9,980,951 B2 | 5/2018 | Schultz et al. |
| 2008/0032940 A1 | 2/2008 | Kalyanaraman et al. |
| 2011/0053938 A1 | 3/2011 | Foley et al. |
| 2014/0112873 A1 | 4/2014 | Gillies et al. |
| 2014/0128380 A1 | 5/2014 | Blaskovich et al. |
| 2015/0038434 A1 | 2/2015 | Yang et al. |
| 2015/0119341 A1 | 4/2015 | Yang et al. |
| 2015/0284431 A1 | 10/2015 | Cai et al. |
| 2016/0046688 A1 | 2/2016 | Perricone et al. |
| 2016/0136309 A1 | 5/2016 | Rosch et al. |
| 2018/0214402 A1 | 8/2018 | Schultz et al. |
| 2019/0321495 A1 * | 10/2019 | Schultz ................. A61K 31/519 |

FOREIGN PATENT DOCUMENTS

| | | | |
|---|---|---|---|
| CN | 104974745 A | 10/2015 | |
| EP | 1847274 A1 * | 10/2007 | ........... A61K 31/192 |
| EP | 1574213 B1 * | 7/2008 | ........... A61K 31/165 |
| EP | 2698156 A1 | 2/2014 | |
| WO | 1993015733 A1 | 8/1993 | |
| WO | 1993021963 A2 | 11/1993 | |

(Continued)

OTHER PUBLICATIONS

Jordan et al., "Vemurafenib for the treatment of melanoma", 2012, Expert Opinion on Pharmacotherapy, 13(17), pp. 2533-2543. (Year: 2012).*
Goodall et al., "Development of potent autophagy inhibitors that sensitize oncogenic BRAF V600E mutant melanoma tumor cells to vemurafenib", 2014, Autophagy, 10(6), pp. 1120-1136. (Year: 2014).*
Manic et al., "Chloroquine and hydroxychloroquine for cancer therapy", Mol. Cell. Oncol., Jul. 15, 2014;1(1):e29911. doi: 10.4161/mco.29911. (Year: 2014).*
Aykin-Burns, et al., "Increased levels of superoxide and H2O2 mediate the differential susceptibility of cancer cells versus normal cells to glucose deprivation", Biochem J, 418(1), 29-37 (2009).
Chen, "Mitochondrial membrane potential in living cells", Ann Rev Cell Biol 4, 155-181 (1988).

(Continued)

*Primary Examiner* — My-Chau T. Tran
(74) *Attorney, Agent, or Firm* — Viksnins Harris Padys Malen LLP

(57) ABSTRACT

The invention provides compositions and methods to treat a hyperproliferative disorder with phenyl butyric acid (PBA) or a pharmaceutically acceptable salt thereof and an anti-cancer composition.

15 Claims, 9 Drawing Sheets

(56) References Cited

FOREIGN PATENT DOCUMENTS

Figure 1:
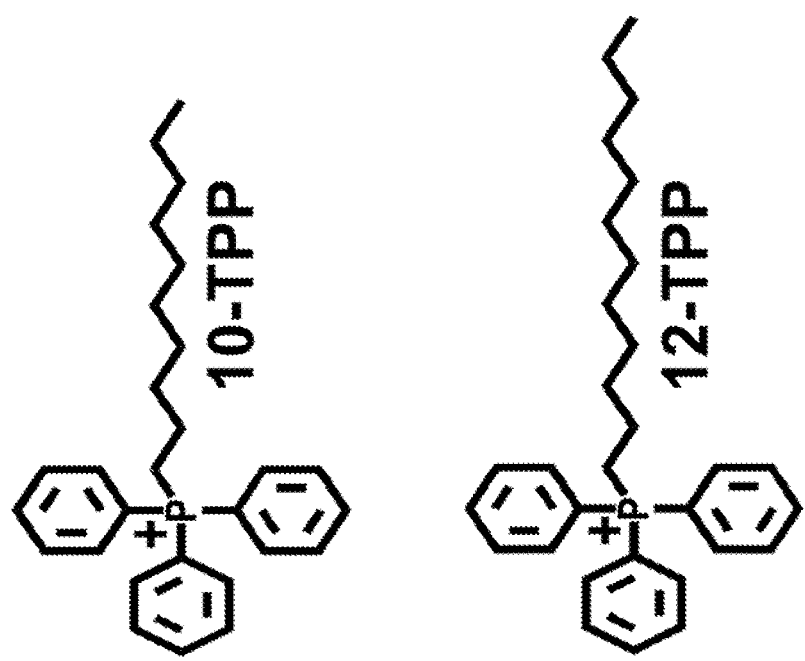
Figure 1:
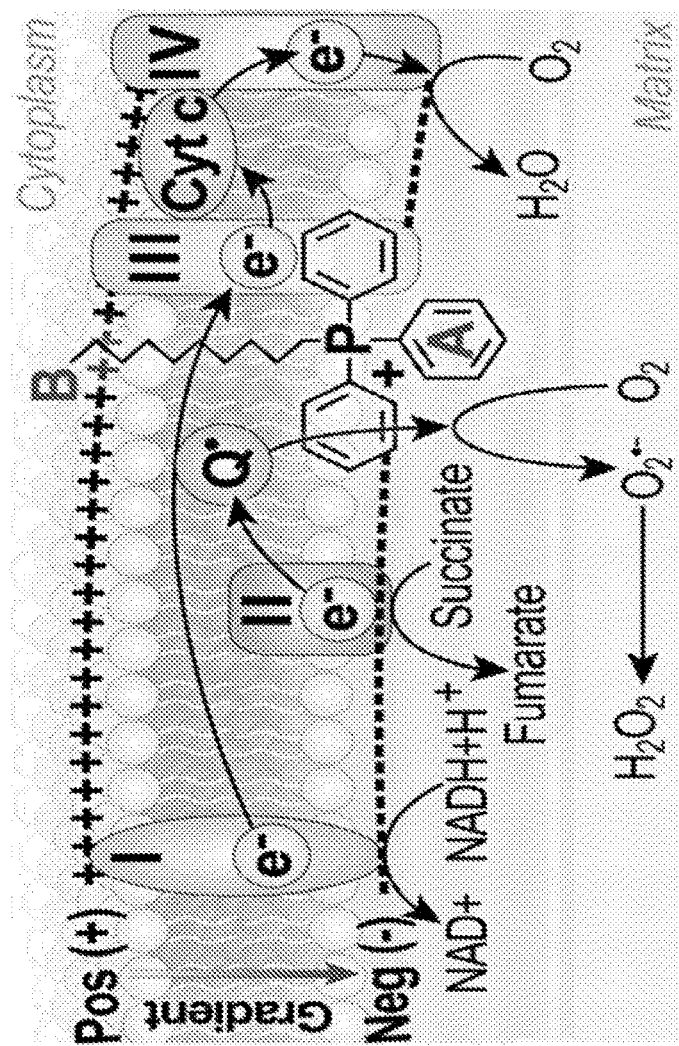

| WO | WO-2005023179 A2 * | 3/2005 | ........... A61K 9/0019 |
|---|---|---|---|
| WO | 2013019975 A1 | 2/2013 | |
| WO | 2014072493 A1 | 5/2014 | |
| WO | 2014124384 A1 | 8/2014 | |

OTHER PUBLICATIONS

Lai, et al., "Histone Deacetylases (HDACs) as Mediators of Resistance to Apoptosis in Melanoma and as Targets for Combination Therapy with Selective BRAF Inhibitors", Advances in Pharmacology 65, ISSN 1054-3589, 27-43 (2012).

Lee, "GRP78 induction in cancer: therapeutic and prognostic implications", Cancer Res 67, 3496-3499 (2007).

Little, et al., "A New Combination Therapy for Metastatic Melanoma", University of Iowa Summer Undergraduate Research Day, University of Iowa, Iowa City, IA (2015).

Malo, et al., "4-Phenylbutyric acid reduces endoplasmic reticulum stress, trypsin activation, and acinar cell apoptosis while increasing secretion in rat pancreatic acini", Pancreas 42, 92-101 (2013).

Misra, et al., "The role of Grp 78 in alpha 2-macroglobulin-induced signal transduction. Evidence from RNA interference that the low density lipoprotein receptor-related protein is associated with, but not necessary for, GRP 78-mediated signal transduction", J Biol Chem. 277(44), 42082-42087 (2002).

Patent Cooperation Treaty, International Searching Authority, Search Report and Written Opinion for PCT/US2016/43993, 13 pages, dated Oct. 4, 2016.

Zain, et al., "Targeting Histone Deacetyalses in the Treatment of B-and T-cell Malignancies", Invest New Drugs 28 (Suppl 1), S58-S78 (2010).

Ackerman, A , et al., "Outcomes of patients with metastatic melanoma treated with immunotherapy prior to or after BRAF inhibitors", Cancer 120(11), 1695-1701 (2014).

Adekola, K , et al., "Glucose transporters in cancer metabolism", Curr. Opin. Oncol. 24(6), 650-654 (2012).

Ahmad, I , et al., "Mitochondrial O2*- and H2O2 mediate glucose deprivation-induced stress in human cancer cells", J Biol Chem 280,4254-4263 (2005).

Asundi, J , et al., "MAPK Pathway Inhibition Enhances the Efficacy of an Anti-Endothelin B Receptor Drug Conjugata by Inducing Target Expression in Melanoma", Mol Cancer Ther 13 (6), 1599-1610 (2014).

Beaino, W , et al., "PET Imaging of Very Late Antigen-4 in Melanoma: Comparison of 68Ga- and 64Cu-Labeled NODAGA and CB-TE1A1P-LLP2A Conjugates", J Nucl Med 55, 1856-1863 (2014).

Birch-Machin, M , et al., "An evaluation of the measurement of the activities of complexes I-IV in the respiratory chain of human skeletal muscle mitochondria", Biochem Med Metab Biol 51(1), 35-42 (1994).

Bradford, M , et al., "A rapid and sensitive method for the quantitation of microgram quantities of protein utilizing the principle of protein-dye binding", Anal Biochem 72, 248-254 (1976).

Burkitt, K , et al., "Phenylbutyrate interferes with the Fanconi anemia and BRCA pathway and sensitizes head and neck cancer cells to cisplatin", Molecular Cancer 7(24), 9 pages (2008).

Cecil Textbook of Medicine , Cecil Textbook of Medicine, 20th Edition, vol. 1 (1996).

Dai, J. , et al., "Malignant Cells Can Be Sensitized to Undergo Growth Inhibition and Apoptosis by Arsenic Trioxide Through Modulation of the Glutathione Redox System", Blood, vol. 93, No. 1, 268-277 (1999).

Ding, D , et al., "Bioprobes based on AIE fluorogens", Acc. Chem. Res. 46(11), 2441-2453 (2013).

Fath, M , et al., "Enhancement of carboplatin-mediated lung cancer cell killing by simultaneous disruption of glutathione and thioredoxin metabolism", Clin Cancer Res 17 (19), 6206-6217 (2011).

Fath, M , et al., "Mitochondrial electron transport chain blockers enhance 2-deoxy-D-glucose induced oxidative stress and cell killing in human colon carcinoma cells", Cancer Biol Ther 8(13), 1228-1236 (2009).

Figg, W , et al., "In vitro antitumor effect of hydroxyurea on hormone-refractory prostate cancer cells and its potentiation by phenylbutyrate", Anti-Cancer Drugs 5, 336-342 (1994).

Gabr, M , et al., "Synthesis and aggregation-induced emission properties of pyridine and pyridinium analogues of tetraphenylethylene", RSC Adv 5, 90226-90234 (2015).

Gius, D , et al., "Redox signaling in cancer biology", Antioxid Redox Signal 8(7-8), 1249-1252 (2006).

Gore, S , "In vitro basis for treatment with hypomethylating agents and histone deacetylase inhibitors: can epigenetic changes be used to monitor treatment÷", Leukemia Research 33 Suppl 2, S2-S6 (2009).

Griffith, O , et al., "Determination of glutathione and glutathione disulfide using glutathione reductase and 2-vinylpyridine", Anal Biochem 106, 207-212 (1980).

Gura , "Systems for Identifying New Drugs are Often Faulty", Science 278 (5340), 1041-1042 (1997).

Han, H , et al., "The rational design of a gemcitabine prodrug with AIE-based intracellular light-up characteristics for selective suppression of pancreatic cancer cells", Chem Commun (Camb). 51(98):17435-17438 (2015).

Howlader, N , et al., "SEER Cancer Statistics Review, 1975-2014", National Cancer Institute. Bethesda, MD, https://seer.cancer.gov/csr/1975_2014/, based on Nov. 2016 SEER data submission, posted to the SEER web site, Apr. 2017.

Hu, Q , et al., "Mitochondria-targeted cancer therapy using a light-up probe with aggregation-induced-emission characteristics", Angew. Chem. Int. Ed. Engl. 53(51), 14225-14229 (2014).

Indran, I , et al., "Recent advances in apoptosis, mitochondria and drug resistance in cancer cells", Biochim. Biophys. Acta 1807(6), 735-745 (2011).

Johnson, J , et al., "Relationships between drug activity in NCI preclinical in vitro and in vivo models and early clinical trials", British J of Cancer 84, 1424-1431 (2001).

Leung, C , et al., "A photostable AIE luminogen for specific mitochondrial imaging and tracking", J. Am. Chem. Soc. 135(1), 62-65 (2013).

Lin, X , et al., "2-Deoxy-D-glucose-induced cytotoxicity and radiosensitization in tumor cells is mediated via disruptions in thiol metabolism", Cancer Res. 63 (12), 3413-3417 (2003).

Liu , et al., "A Small-Molecule Inhibitor of Glucose Transporter 1 Downregulates Glycolysis, Induces Cell-Cycle Arrest, and Inhibits Cancer Cell Growth in Vitro and in Vivo", Molecular Cancer Therapy, 11(8), 1672-1682 (2012).

Lowry, O , "Protein measurement with the Folin phenol reagent", J Biol Chem 193(1), 265-275 (1951).

Martin, M , et al., ""Click" cyclized gallium-68 labeled peptides for molecular imaging and therapy: Synthesis and preliminary in vitro and in vivo evaluation in a melanoma model system", Recent Results Cancer Res 194, 149-175 (2013).

Millard, Melissa , et al., "Preclinical Evaluation of Novel Triphenylphosphonium Salts with Broad-Spectrum Activity", PLoS One vol. 5 (10), e13131, 1-18 (2010).

Modica-Napolitano, J , et al., "Delocalized lipophilic cations selectively target the mitochondria of carcinoma cells", Adv. Drug Delivery Rev. 49(1-2), 63-70 (2001).

Mueckler, M , "Facilitative glucose transporters", Eur. J. Biochem. 219(3), 713-725 (1994).

Murphy, M , et al., "Drug delivery to mitochondria: the key to mitochondrial medicine", Adv. Drug Delivery Rev. 41(2), 235-250 (2000).

Murphy, M , "How mitochondria produce reactive oxygen species", Biochem J 417(1), 1-13 (2009).

Murphy, M , et al., "Targeting antioxidants to mitochondria by conjugation to lipophilic cations", Annu. Rev. Pharmacol. Toxicol. 47, 629-656 (2007).

Murphy, M , "Targeting lipophilic cations to mitochondria", Biochim. Biophys. Acta 1777 (7-8), 1028-1031 (2008).

(56) References Cited

OTHER PUBLICATIONS

O'Dwyer, P., et al., "Phase 1 Trial of Buthionine Sulfoximine in Combination with Melphalan in Patients with Cancer", Oncol. vol. 14, No. 1, 249-256 (1996).

Phillips, J., et al., "Pilot study of sodium phenylbutyrate as adjuvant in cyclophosphamide-resistant endemic Burkitt's lymphoma", Transaction of the Royal Society of Tropical Medicine and Hygiene 101, 1265-1269 (2007).

Puck, T., et al., "Action of x-rays on mammalian cells. II. Survival curves of cells from normal human tissues", J Exp Med 106, 485-500 (1957).

Reedy, J., et al., "Synthesis and Evaluation of Tetraarylethylene-based Mono-, Bis-, and Tris(pyridinium) Derivatives for Image-Guided Mitochondria-Specific Targeting and Cytotoxicity of Metastatic Melanoma Cells", Bioconjugate Chem 27, 2424-2430 (2016).

Ripcke, J., et al., "Small-molecule targeting of the mitochondrial compartment with an endogenously cleaved reversible tag", ChemBioChem 10(10), 1689-1696 (2009).

Rohlena, J., et al., "Anticancer drugs targeting the mitochondrial electron transport chain", Antioxid. Redox Signaling 15(12), 2951-2974 (2011).

Schibler, J., et al., "Mitochondrial-Targeted DecylTriphenylphosphonium Enhances 2-Deoxy-D-Glucose Mediated Oxidative Stress and Clonogenic Killing of Multiple Myeloma Cells", PLOS One 11(11): e0167323 (2016).

Schniewind, B., et al., "Combination phenylbutyrate/gemcitabine therapy effectively inhibits in vitro and in vivo growth of NSCLC by intrinsic apoptotic pathways", Journal of Carcinogenesis 5(25), 11 pages (2006).

Simons, A., et al., "Glucose deprivation-induced metabolic oxidative stress and cancer therapy", J. Cancer Res. Ther. 5(Suppl 1) S2, 7 pages (2009).

Simons, A., et al., "Inhibition of glutathione and thioredoxin metabolism enhances sensitivity to perifosine in head and neck cancer cells", J Oncol 2009, 519563, 10 pages (2009).

Smith, R., et al., "Animal and human studies with the targeted antioxidant MitoQ", Annals of the New York Academy of Sciences 1201, 96-103 (2010).

Smith, R., et al., "Delivery of Bioactive Molecules to Mitochondria in vivo", PNAS, vol. 100, No. 9, 5407-5412 (2003).

Sousa, R., et al., "Treatment for metastatic melanoma: a new and evolving era", Int J Clin Pract 69(3), 273-280 (2015).

Spitz, D., et al., "Cytotoxicity and metabolism of 4-hydroxy-2-nonenal and 2-nonenal in $H_2O_2$-resistant cell lines. Do aldehydic by-products of lipid peroxidation contribute to oxidative stress?", Biochem J 267, 453-459 (1990).

Spitz, D., et al., "Glucose deprivation-induced oxidative stress in human tumor cells. A fundamental defect in metabolism?", Ann. N. Y. Acad. Sci., 899, 349-362 (2000).

Tolk, H., et al., "Complete remission of metastatic melanoma upon BRAF inhibitor treatment—what happens after discontinuation?", Melanoma Res 25(4), 362-366 (2015).

Tong, H., et al., "Fluorescent "light-up" bioprobes based on tetraphenylethene derivatives with aggregation-induced emission characteristics", Chem Commun 35, 3705-3707 (2006).

Trnka, J., et al., "Lipophilic triphenylphosphonium cations inhibit mitochondrial electron transport chain and induce mitochondrial proton leak", PLoS One 10(4), e0121837, 14 pages (2015).

Tseng, W., et al., "Long-term survivors after immunotherapy for metastatic melanoma", Immunol Lett 139(1-2), 117-118 (2011).

Wang, Z., et al., "Long-term fluorescent cellular tracing by the aggregates of AIE bioconjugates", J. Am. Chem. Soc. 135(22), 8238-8245 (2013).

Yuan, H., et al., "Fluorescent and radiolabeled triphenylphosphonium probes for imaging mitochondria", Chem. Commun. 49 (88), 10361-10363 (2013).

Zhang, G., et al., "General Synthetic Approach toward Geminal-Substituted Tetraarylethene Fluorophores with Tunable Emission Properties: X-ray Crystallography, Aggregation-Induced Emission and Piezofluorochromism", Chemistry Materials 26(15), 4433-4446 (2014).

\* cited by examiner

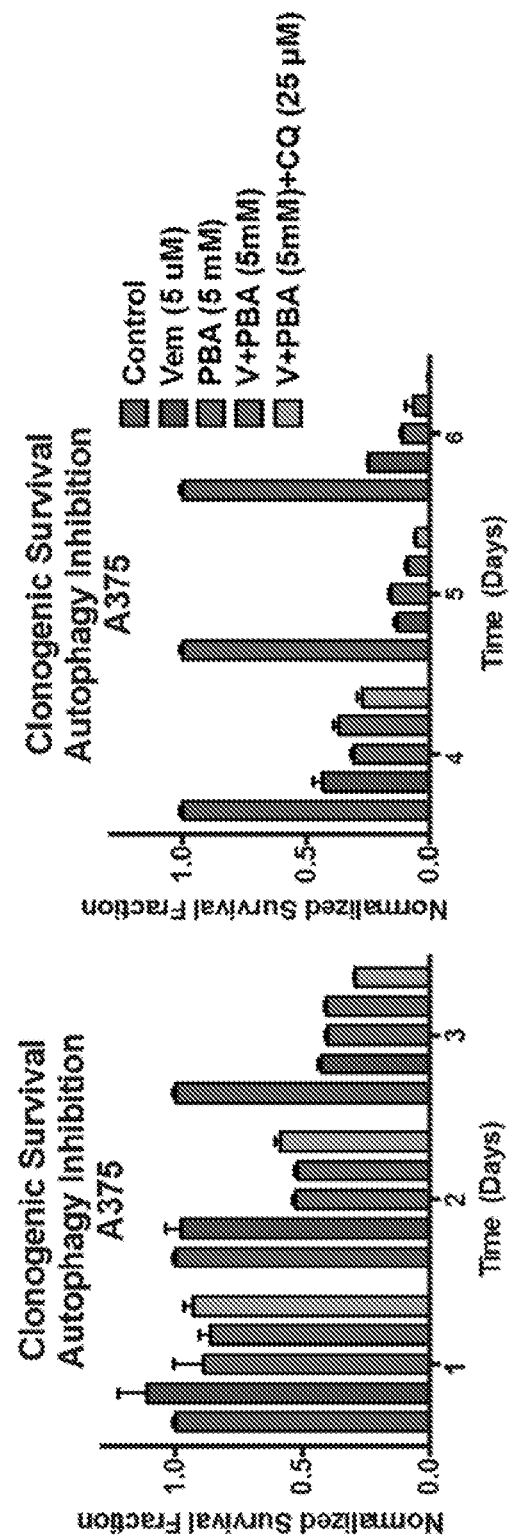

COMPOSITIONS AND METHODS FOR TREATING CANCER

RELATED APPLICATIONS

This application claims priority to U.S. Provisional Patent Application Nos. 62/198,001 filed Jul. 28, 2015, and 62/241,379 filed Oct. 14, 2015, the entirety of which are incorporated herein by reference.

FEDERAL GRANT SUPPORT

The invention was made with government support under 1K25CA172218-01A1 awarded by the National Institutes of Health and 2012-DN-130-NF0001 awarded by the Department of Homeland Security. The government has certain rights in the invention.

BACKGROUND

Melanoma is a cancer of the skin and is the fastest growing cancer incidence in the world today. Disease detected early can be removed by surgery, but when melanoma spreads to other parts of the body (called metastatic melanoma) it is almost uniformly fatal. The reason for this is that metastatic melanoma rapidly becomes resistance to all forms of treatment. The first new therapy that appeared effective for melanoma was approved in 2011. The pharmaceutical called vemurafenib targets patients with a gene mutation ($BRAF^{V600E}$) that is present in about half of melanoma patients. Although these patients respond well to the treatment, melanoma develops resistance to the therapy rapidly. Thus, the new therapy, which initially was heralded as the end of melanoma, extends life expectancy by only months with severe side effects. Vemurafenib is one of several BRAF inhibitors that are being used for melanoma therapy that target the BRAF protein. Melanoma develops resistance to all of these therapies. Several other drugs that have different mechanisms of action are also approved for melanoma treatment, but the disease eventually develops resistance to all therapies for melanoma. There is no treatment for metastatic melanoma that overcomes resistance of melanoma cancer cells, which leads to a high mortality rate.

Thus, there is a continuing need for compositions and methods for the treatment of melanoma in animals (e.g., humans). Combination therapies that overcome resistance mechanisms that arise in almost all melanoma patients are particularly needed.

SUMMARY

In certain embodiments, the present invention provides a combination of phenyl butyric acid (PBA) or a pharmaceutically acceptable salt thereof; and one or more anti-cancer compositions for the therapeutic treatment of a hyperproliferative disorder. As a combined treatment the combination treatment effectively destroys metastatic melanoma cancer cells.

In certain embodiments, the hyperproliferative disorder is cancer. In certain embodiments, the cancer is drug-resistant. As used herein, the term "drug-resistant" is reduction in effectiveness of a drug in killing malignant cells; reducing cancerous tumor size and rate of growth; and ameliorating the disease or condition. In certain embodiments, the drug's effectiveness is reduced by at least about 10%, 20%, 30%, 40%, 50%, 60%, 70%, 80%, 90%, or even 100%, as compared to its effects when first administered to the mammal.

In certain embodiments, the cancer is melanoma. In certain embodiments, the melanoma is resistant to vemurafenib treatment.

In certain embodiments, the PBA or a pharmaceutically acceptable salt thereof is administered simultaneously with the anti-cancer composition.

In certain embodiments, the PBA or a pharmaceutically acceptable salt thereof and the anti-cancer composition are administered sequentially.

In certain embodiments, the administration of the anti-cancer composition begins about 1 to about 10 days before administration of the PBA or a pharmaceutically acceptable salt thereof.

In certain embodiments, the administration of the PBA or a pharmaceutically acceptable salt thereof begins about 1 to about 10 days before administration of the anti-cancer composition.

In certain embodiments, the administration of the PBA or a pharmaceutically acceptable salt thereof and administration of the anti-cancer composition begins on the same day and/or simultaneously.

In certain embodiments, the anti-cancer composition comprises vemurafenib.

In certain embodiments, the anti-cancer composition comprises chloroquine (or hydrochloroquin). In certain embodiments, the anti-cancer composition comprises a derivative of triphenylphosphonium (TPP), or a pharmaceutically acceptable salt thereof.

In certain embodiments, the anti-cancer composition comprises is ipilimumab.

In certain embodiments, the PBA or a pharmaceutically acceptable salt thereof is administered in combination with vemurafenib, and the cancer is melanoma.

In certain embodiments, the PBA or a pharmaceutically acceptable salt thereof is administered in combination with vemurafenib and chloroquine (or hydrochloroquin), and the cancer is melanoma.

In certain embodiments, the present invention provides a use of the combination of PBA or a pharmaceutically acceptable salt thereof and anti-cancer composition in the preparation of a medicament for the treatment of a hyperproliferative disorder in a mammal.

In certain embodiments, the present invention provides a kit comprising PBA or a pharmaceutically acceptable salt thereof, a container, and a package insert or label indicating the administration of the PBA or a pharmaceutically acceptable salt thereof with an anti-cancer composition for treating a hyperproliferative disorder.

In certain embodiments, the present invention provides a product comprising PBA or a pharmaceutically acceptable salt thereof, and an anti-cancer composition; as a combined preparation for separate, simultaneous or sequential use in the treatment of a hyperproliferative disorder.

In certain embodiments, the present invention provides a method for treating a hyperproliferative disorder in a mammal, comprising administering to the mammal a combination of PBA or a pharmaceutically acceptable salt thereof; and an anti-cancer composition.

In certain embodiments, the PBA or a pharmaceutically acceptable salt thereof is administered for more than a month.

In certain embodiments, the PBA or a pharmaceutically acceptable salt thereof is administered for more than a year.

In certain embodiments, the PBA or a pharmaceutically acceptable salt thereof is administered at a dosage of at least 500 mg/day.

In certain embodiments, the PBA or a pharmaceutically acceptable salt thereof is administered at a dosage of at least 1500 mg/day.

In certain embodiments, the PBA or a pharmaceutically acceptable salt thereof is administered via hose dose venous infusion to achieve a constant blood concentration of at least 0.1 mM.

In certain embodiments, the present invention provides a use of PBA or a pharmaceutically acceptable salt thereof; and an anti-cancer composition for the therapeutic treatment of a hyperproliferative disorder. In certain embodiments, the hyperproliferative disorder is cancer. In certain embodiments, the cancer is melanoma.

In certain embodiments, the PBA or a pharmaceutically acceptable salt thereof is administered in combination with an anti-cancer composition.

In certain embodiments, in the use:

a) PBA or a pharmaceutically acceptable salt thereof is administered simultaneously with the anti-cancer composition; or b) PBA or a pharmaceutically acceptable salt thereof and the anti-cancer composition are administered sequentially; or c) administration of the an anti-cancer composition begins about 1 to about 10 days before administration of the one or more anti-cancer agents; or d) administration of PBA or a pharmaceutically acceptable salt thereof begins about 1 to about 10 days before administration of the anti-cancer composition; or e) administration of PBA or a pharmaceutically acceptable salt thereof and administration of the anti-cancer composition begins on the same day.

In certain embodiments, the PBA or a pharmaceutically acceptable salt thereof is administered in combination with vemurafenib, and the cancer is melanoma.

BRIEF DESCRIPTION OF THE DRAWINGS AND TABLES

FIG. 1: Proposed Mechanism of TPP-drug induced oxidative stress. The positively charged TPP head (A) preferentially translocates TPP to the mitochondrial membrane due to the hyperpolarized membrane gradient in cancer cell mitochondria; The side chain (B) (a 10 carbon aliphatic 10-TPP shown here) embeds into the inner mitochondrial membrane, disrupting ETC complexes (drawn here at complex III) leading to increased levels of superoxide and hydrogen peroxide. Structures of 10-TPP and 12-TPP are also provided.

Figure 2:
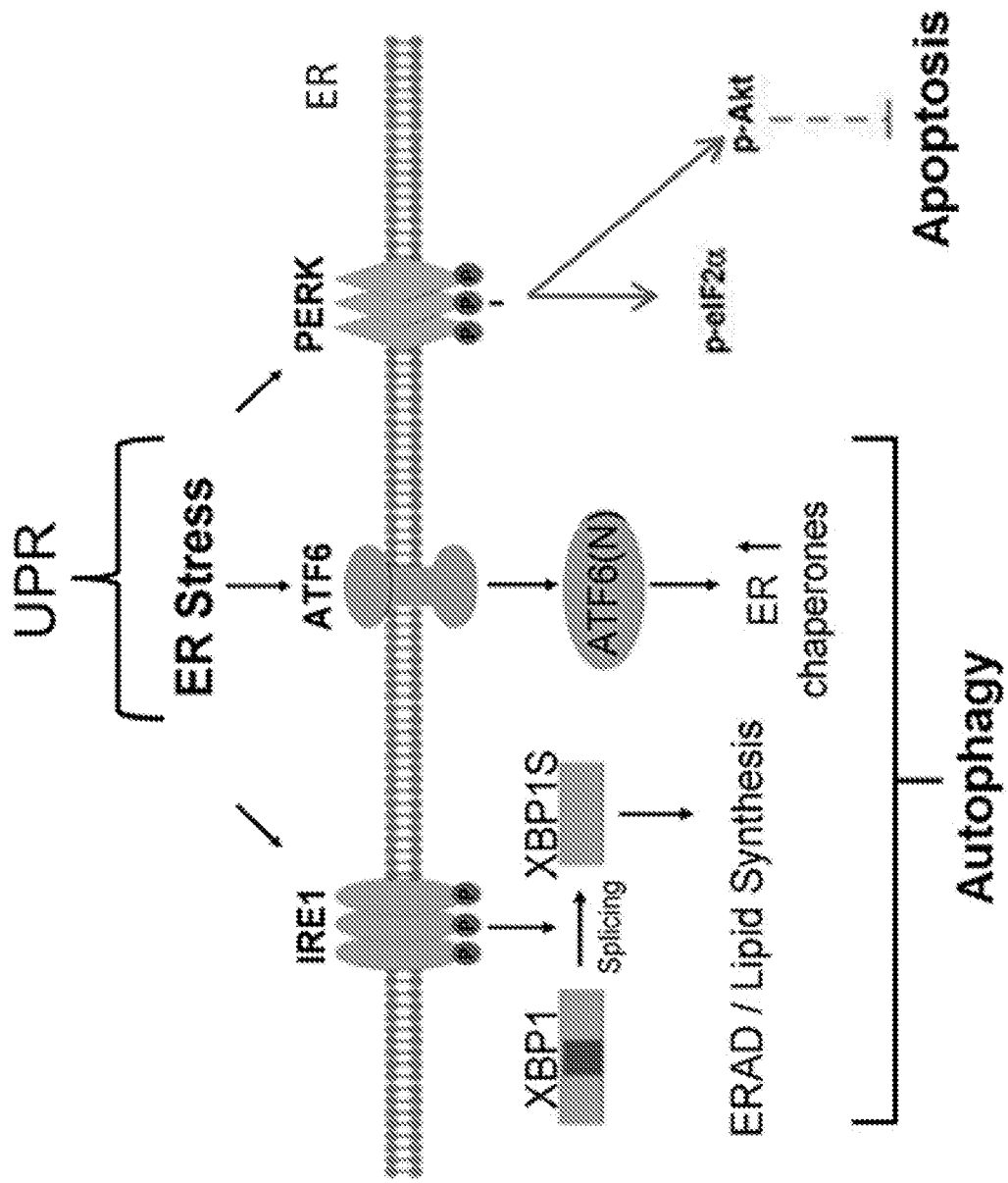

FIG. 2: Schematic representation of UPR. Under conditions of redox imbalance and nutrient stress, protein folding machinery is perturbed, which leads to the accumulation of mis-folded proteins in the ER and subsequent ER stress. To manage ER stress, BiP (an ER resident molecular chaperone) initiates the UPR by activating IRE1, PERK and ATF6 mediated signaling pathways. These pathways reduce ER stress through increased expression of UPR related genes and molecular chaperones (ATF6 pathway); through activated ER associated protein degradation (ERAD) (IRE1 pathway) to reduce ER protein load; and through reduced mRNA translation and autophagy in order to clear misfolded protein aggregates via the formation of autophagosomes (PERK pathway). If the ER stress cannot be reduced, UPR signaling pathways mediate the activation of apoptosis. Amy S. Lee, *Cancer Res* (2007); 77:3496-3499.

Figures 3A, 3B:
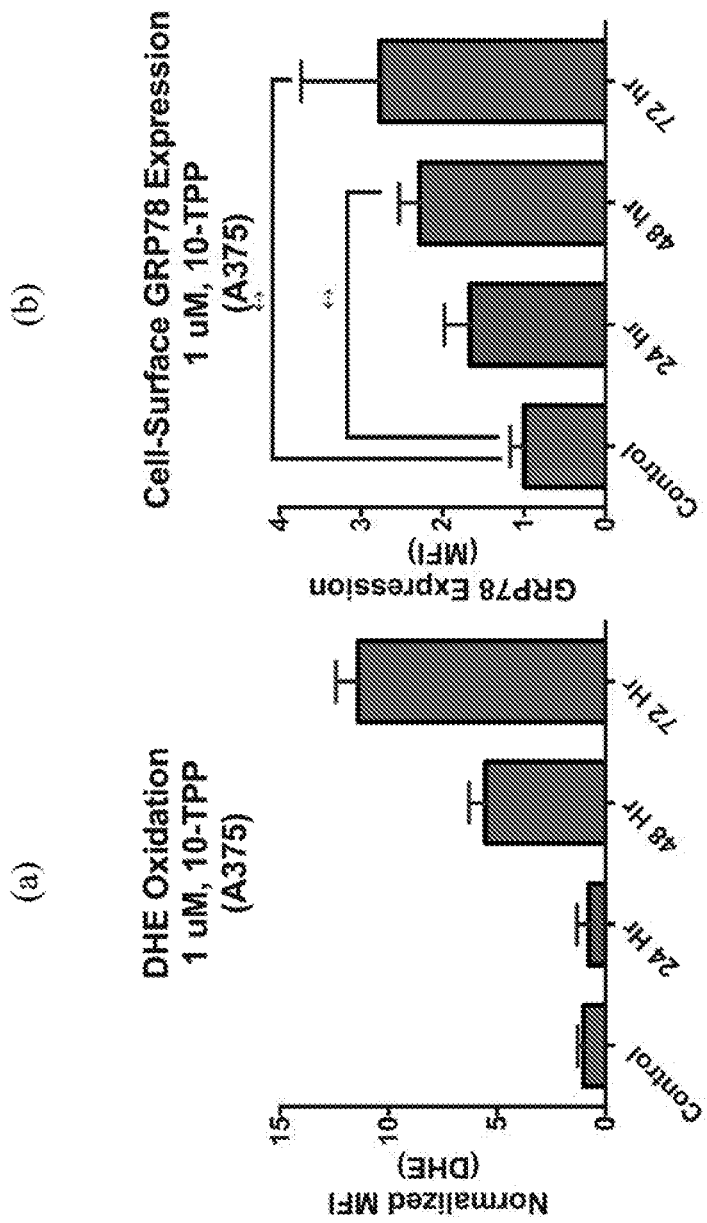

FIGS. 3A-3B: 10-TPP increases ROS production and cell-surface expression of GRP78—an ER stress marker. a) Dihydroethidium (DHE) is a fluorescent marker used to evaluate reactive oxygen species (ROS) production. In this experiment, we wanted to determine if 10-TPP increases cellular ROS levels. A375 cells were treated with 1 μM 10-TPP for 24 h, 48 h, and 72 h. Cells were then incubated with DHE and analyzed by flow cytometry. Results demonstrate that DHE oxidation increases with increased 10-TPP treatment length, indicating increased production levels of ROS and subsequent oxidative and ER stress. b) Glucose regulated protein GRP78 is an ER resident protein. Under conditions of stress (ER stress, oxidative stress) it translocates to the cell surface. Uma K. Misra et. al., *Journal of Biological Sciences* (2002), Vol. 277, No. 44, 42082-42089. We analyzed the cell surface expression of GRP78 as a marker of ER stress in A375 cells treated with 1 μM 10-TPP for 24 h, 48 h, and 72 h. Following treatment, cells were harvested, labelled with Alexa-488 tagged GRP78 antibody, and analyzed by flow cytometry. Results demonstrate that GRP 78 expression increases in cells treated with 10-TPP and that expression increases with the length of 10-TPP treatment time. Collectively, these results demonstrate that 10-TPP increases oxidative and ER stress, and that increased stress results in increased GRP 78 cell-surface expression.

Figure 4A:
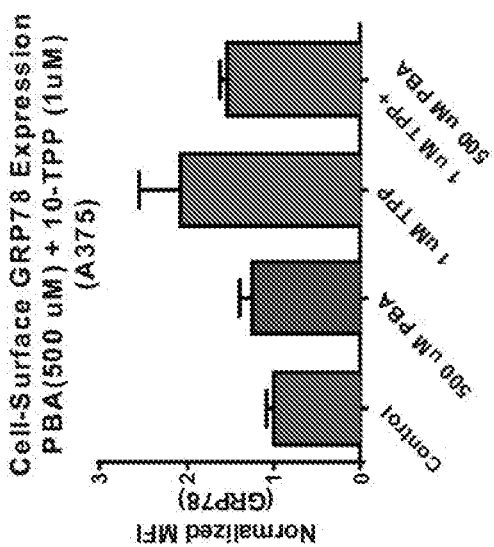
Figure 4B:
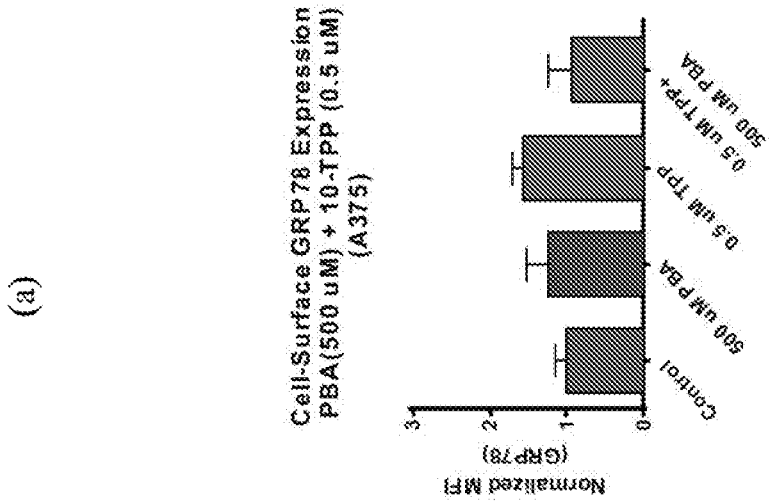
Figures 5A, 5B:
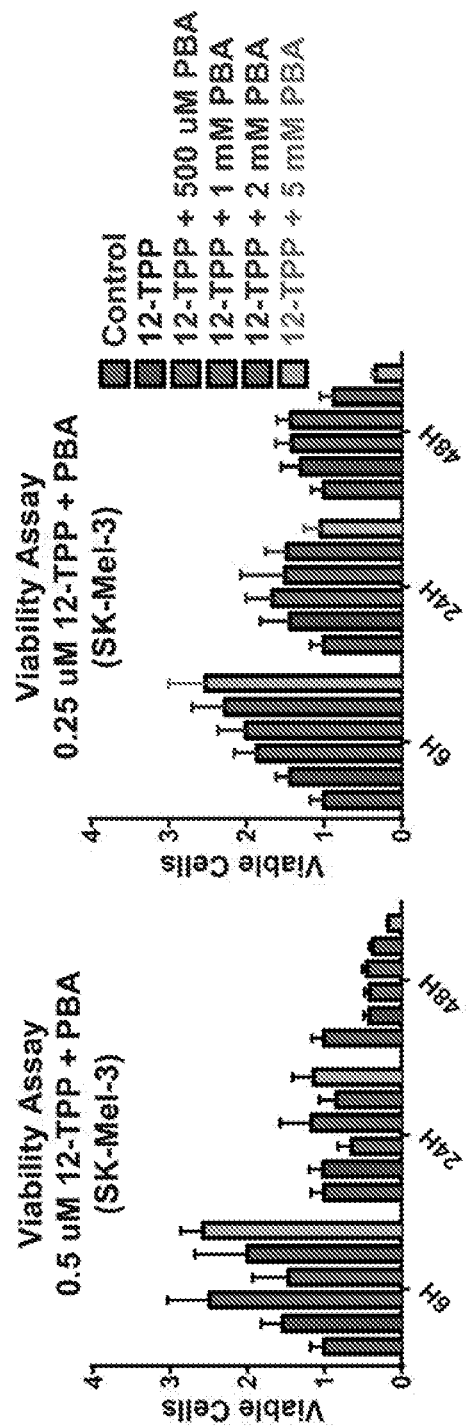

FIGS. 4A-4B: PBA and 10-TPP decreases ER stress levels and clonogenic survival in a time and concentration dependent manner. Malo A et al., *Pancreas* (2013). Mar 42 (2):388. a) 4-phenyl butyric acid is known to bind with free nitrogen and therefore has the ability act as a chemical molecular chaperone. This experiment demonstrates the ability of PBA to decrease ER-stress. A375 cells were treated with PBA and 10-TPP respectively for 48 hours. Our results demonstrate a decrease in the expression of cell-surface GRP78 when treated with 0.5 μM and 1 μM 10-TPP in combination with PBA. b) This result shows a decrease in the clonogenic survival of A375 melanoma cells when treated with the combination of 10-TPP (0.5 μM, 1 μM) and PBA (100 μM, 500 μM and 1 mM) demonstrating the protective nature of ER stress FIGS. 5A-5B: Combination treatment with 12-TPP and PBA decreases the ER stress and increases 12-TPP toxicity. Viability of cells was analyzed post treatment of melanoma cells with 12-TPP and PBA (reduces ER stress). This result shows a decrease in the viability of SK-Mel-3 melanoma cells when treated with 0.5 μM (FIG. 5A) and 0.25 μM (FIG. 5B) 12-TPP alone along with combination concentrations of PBA (500 μM, 1 mM, 2 mM, and 5 mM) for 6 h, 48 h and 72 h demonstrating the protective nature of ER stress. In each experiment the treatments were as follows (from left to right): Control, 12-TPP, 12-TPP+500 μM PBA, 12-TPP+1 mM PBA, 12-TPP+2 mM PBA, or 12-TPP+5 mM PBA.

Figure 6:
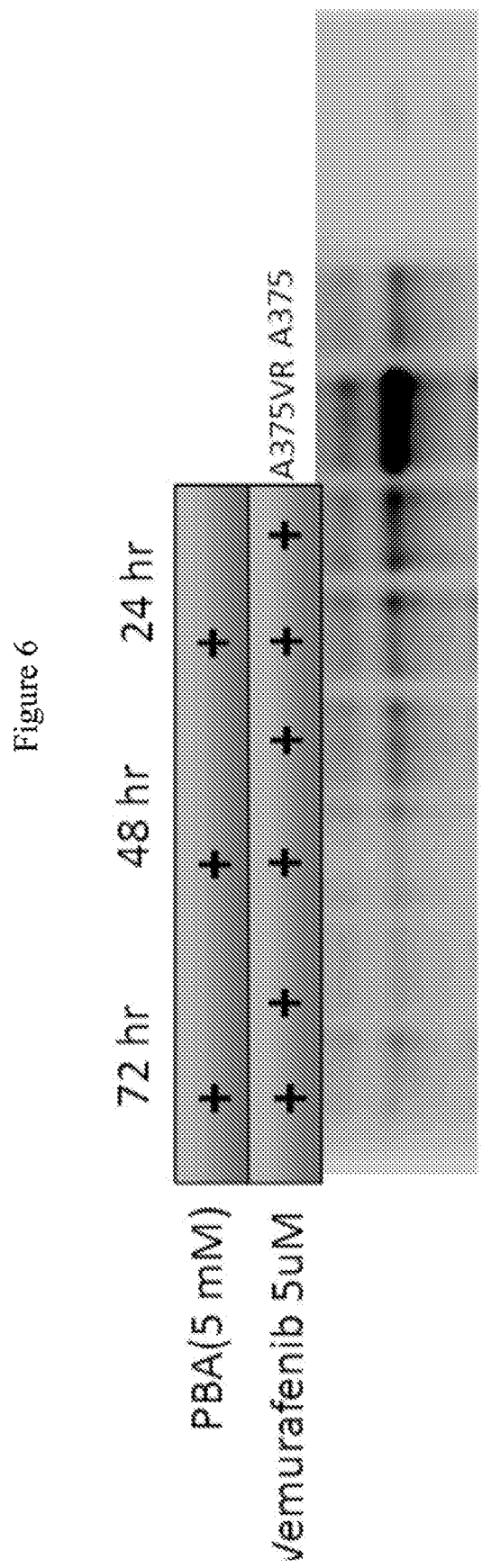

FIG. 6: PBA reduces ER stress.

Figure 7:
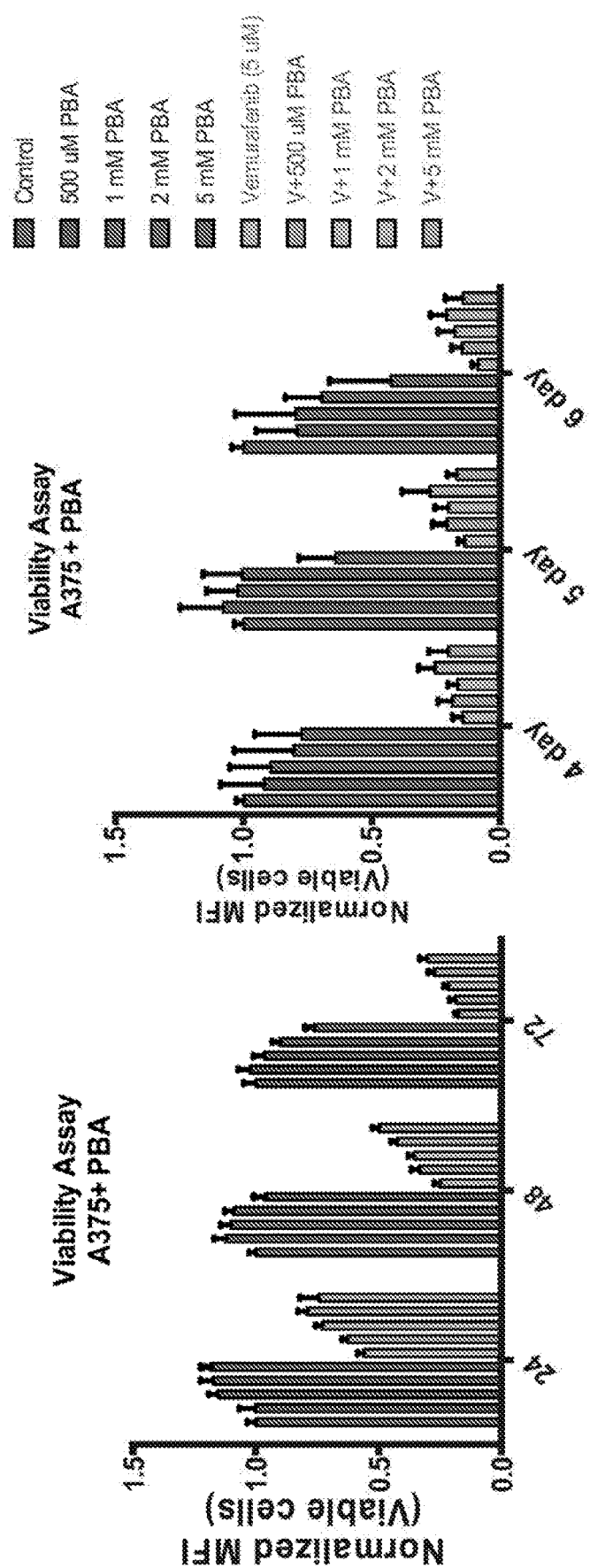

FIG. 7: PBA combined with vemurafenib decreases the survival of vemurafenib Sensitive A375 melanoma cells. In each experiment the concentration in each treatment was as follows (from left to right): Control, 500 μM PBA, 1 mM PBA, 2 mM PBA, 5 mM PBA, Vemurafenib (5 μM), Vemurafenib+500 μM PBA, Vemurafenib+1 mM PBA, Vemurafenib+2 mM PBA, or Vemurafenib+5 mM PBA.

Figure 8:
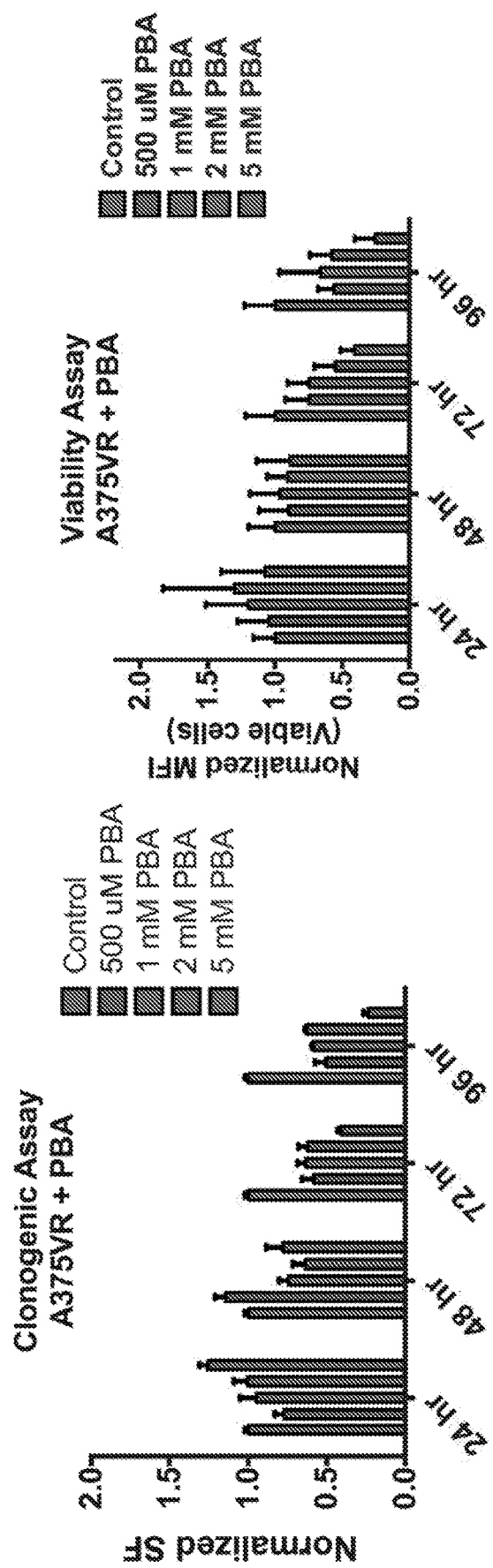

FIG. 8: PBA combined with vemurafenib decreases the survival of vemurafenib desistant A375 Melanoma cells. In each experiment the concentration in each treatment was as follows (from left to right): Control, 500 µM PBA, 1 mM PBA, 2 mM PBA, 5 mM PBA.

FIG. 9: PBA combined with vemurafenib and chloroquine decreases the survival of vemurafenib resistant A375 Melanoma cells to a greater extent than the combination of vemurafenib and PBA.

DETAILED DESCRIPTION

Melanoma is the dangerous type of skin cancer that develops in cells that produce melanin (melanocytes), usually presenting as an irregular spot/mole on the skin. Causes of melanoma include UV radiation and a genetic predisposition to this type of cancer. Unlike other cancers, prevalence of melanoma is increasing, with the highest occurrence among individuals 25-29 years old. The overall lifetime risk of developing melanoma is 2.4%. In 2015, 73,870 new invasive melanomas are expected to be diagnosed, with 9,940 people expected to die of melanoma. With early treatment, survival rate is 97%.

Melanoma can migrate to other parts of the body (metastatic melanoma), and one year survival rate drastically decreases with metastasis—15-20% for Stage IV. Current types of treatment include surgery, immunotherapy (Immune checkpoint inhibitors for advanced melanoma), chemotherapy, radiation therapy, targeted therapy (target cells with gene changes) and BRAF Inhibitors. BRAF is a protein kinase of the mitogen-activated protein kinase (MAPK) pathway, and it regulates cell growth, proliferation, and differentiation. Research suggests a $BRAF^{V600E}$ mutation causes the BRAF protein (produced through the MAPK pathway) to become oncogenic. The mutation may lead to increased and uncontrolled cell proliferation, and resistance to apoptosis. The BRAF mutation is observed in about 50% of melanoma tumors. Its presence is associated with poor prognosis in metastatic melanoma.

Melanoma is the fastest growing cancer incidence in the United States. Surgery is curative for melanoma confined to the skin, but metastatic melanoma is lethal. Current FDA approved therapies for metastatic melanoma (e.g., Vemurafenib, Ipilimumab), have increased life expectancy by months, however resistance develops rapidly. The exact mechanism by which drug resistance develops is unclear; however, autophagy is known to play a major role. Autophagy is a self-degradative response of the cell towards nutrient stress. Conversely, autophagy also plays a housekeeping role by removing mis-folded or aggregated proteins and clearing damaged organelles by forming autophagosomes. Thus, autophagy is believed to play an important role in tumor progression and developing drug resistance during later stages of cancer. The Unfolded Protein Response (UPR) mediated by GRP78 ER associated protein degradation is one of the pathways that initiates autophagy in stressed cells. UPR involves the activation of three signaling pathways mediated by IRE-1, PERK and ATF6. These pathways work towards decreasing the protein load of ER by increasing the expression of molecular chaperons, activation of ERAD (ER associated protein degradation) and autophagy. However if the damage caused by the stress is extensive UPR signaling pathways initiate apoptosis. Amy S. Lee, Cancer Res (2007); 77:3496-3499. Emerging evidence shows that in malignant cells ER stress can be pro-survival and contribute to the development of drug resistance by initiating autophagy.

A new combination therapy has been developed that kills vemurafenib resistant cells, but is virtually non-toxic to the rest of the body.

Phenylbutyrate, and Salts Thereof

As used herein, the term "Phenylbutyrate and salts thereof" includes salts of Phenylbutyrate. PBA has the following structure:

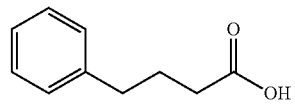 [SMILES: O=C(O)CCCc1ccccc1]

In certain embodiments, Phenylbutyrate is Buphenyl® (sodium phenylbutyrate). Sodium phenylbutyrate is used for chronic management of urea cycle disorders (UCDs). Its mechanism of action involves the quick metabolization of sodium phenylbutyrate to phenylacetate. Phenylacetate then conjugates with glutamine (via acetylation) to form phenylacetylglutamine, and phenylacetylglutamine is excreted by the kidneys. It has been observed that sodium phenylbutyrate reduces Endoplasmic Reticulum (ER) stress.

The cellular response to ER stress is neither fully oncogenic nor completely tumor suppressive. It involves complex signaling with many pathways. The relative importance of each pathway varies between cells depending on chronicity of ER stress, and on relative expression of various associated proteins. As solid cancers grow, nutrients and oxygen required exceed capacity of existing vascular bed, which can trigger angiogenesis (development of new blood vessels) to get more oxygen/nutrients to the cancers. Cancers, however, usually become hypoxic and nutrient-depleted, and with the hypoxia leading to impaired generation of ATP. The low ATP levels compromise ER protein folding which leads to ER stress. Thus, unfolded, and/or misfolded proteins are associated with ER stress and cancer cells exist with higher levels of ER stress relative to health cells.

Potential outcomes as a consequence of ER stress include high rates of protein synthesis that would trigger increased expression of autophagy, which is cytoprotective during stress (liberates amino acids, and removes damaged organelles). Another outcome would be an increased tolerance to hypoxia, which would promote tumor growth. This would also increase autophagy, promoting drug resistance. Thus, a successful treatment would inhibit autophagy and promote cell death.

Sodium phenylbutyrate decreases ER Stress. Lowering ER stress prevents tolerance to hypoxia, and prevents cytoprotective autophagy (which leads to drug resistance). Phenylbutyrate acts as a "chemical chaperone," meaning it guides proper protein folding, and the presence of properly folded proteins lowers ER stress.

Anti-Cancer Agents

As used herein, the term "anti-cancer agent" includes therapeutic agents that kill cancer cells; slow tumor growth and cancer cell proliferation; and ameliorate or prevent one or more of the symptoms of cancer.

For example, the term "anti-cancer agent" includes vemurafenib and triphenylphosphonates (TPP). Vemurafenib (Zelboraf®) is a cancer growth blocker and is a treatment for advanced melanoma.

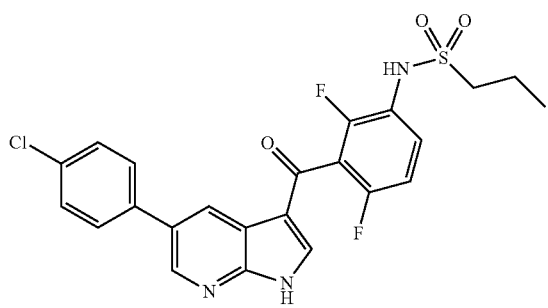 [SMILES: CCCS(=O)(=O)Nc1ccc(F)c(C(=O)c2c[nH]c3ncc(-c4ccc(Cl)cc4)cc23)c1F]

Vemurafenib stops the proliferative effects of oncogenic BRAF protein. The standard method of administration is an oral tablet, administered 4× daily. Unfortunately, metastatic melanoma can resist vemurafenib treatment. Vemurafenib slows tumor progression for only about 5.3 months. As a result, finding an effective treatment for metastatic melanoma is challenging.

For example, the term "anti-cancer agent" includes a Triphenylphosphonium (TPP) agent or derivative thereof that increases reactive oxygen species (ROS) levels in cancer cell mitochondria, and a pharmaceutically acceptable diluent or carrier. As used herein, the term triphenylphosphonium (TPP) is any molecule containing a triphenylphosphine cation ($^+PPh_3$) moiety. See, e.g., WO 2013/019975 and WO 2014/124384, which are incorporated by reference herein.

TPP salts can be reacted with alcohols, alkyl halides, and carboxylic acids, which allow them to be used as starting materials for the synthesis of a large variety of chemical derivatives, e.g., XTPP agents. Charged molecules generally cannot pass through cell membranes without the assistance of transporter proteins because of the large activation energies need to remove of associated water molecules. In the TPP molecules, however, the charge is distributed across the large lipophilic portion of the phosphonium ion, which significantly lowers this energy requirement, and allows the TPP to pass through lipid membranes. The phosphonium salts accumulate in mitochondria due to the relatively highly negative potential inside the mitochondrial matrix. The compositions of the present invention utilize XTPP agents that have activity in treating cancer cells, in that the XTPP agents preferentially localize to cancer cells, as compared to the comparable normal cells because cancer cells are often characterized by abnormal mitochondrial oxidative metabolism (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440) and altered mitochondrial membrane potential (Chen L B: Mitochondrial membrane potential in living cells, Ann. Rev. Cell Biol. 1988; 4:155-81), relative to normal cells.

In certain embodiments, the TTP agent is 10-TTP or 12-TTP (see, FIG. 1).

In certain embodiments, the TTP agent is a compound of formula I:

$Ph_3P^+$-L-W Y$^-$    I wherein:
W is selected from:

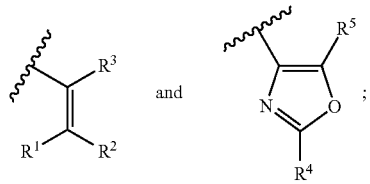

L is absent, $(C_1$-$C_{12})$alkyl, $(C_1$-$C_{12})$alkylene, —$(CH_2CH_2O)_n$M-, —C(=O)NR$^{L1}$—, —NR$^{L1}$C(=O)— or —NR$^{L1}$C(=S)NR$^{L1}$—;
n is 1 to 12;
M is absent or —$CH_2CH_2$—;
R$^{L1}$ is H or $(C_1$-$C_6)$alkyl;
R$^1$ is halo or —NHC(=O)R$_a$;
R$^2$ is halo, SR$_b$, or —C(=O)NHR$_c$;
R$^3$ is —NH(C=O)R$_d$, —NH(C=O)NHR$_d$ or phenyl wherein any phenyl of R$^3$ is optionally substituted with one or more halo, $(C_1$-$C_3)$alkyl, $(C_1$-$C_3)$haloalkyl, O$(C_1$-$C_3)$haloalkyl or —O$(C_1$-$C_3)$alkyl;
R$^4$ is $(C_1$-$C_6)$alkyl or phenyl wherein any phenyl of R$^4$ is optionally substituted with one or more halo, $(C_1$-$C_3)$alkyl, $(C_1$-$C_3)$haloalkyl or —O$(C_1$-$C_3)$alkyl;
R$^5$ is —S$(C_1$-$C_6)$alkyl or —N$((C_1$-$C_6)$alkyl$)_2$;
R$_a$ is phenyl optionally substituted with one or more halo, $(C_1$-$C_3)$alkyl, $(C_1$-$C_3)$haloalkyl or —O$(C_1$-$C_3)$alkyl;
R$_b$ is phenyl optionally substituted with one or more halo, $(C_1$-$C_3)$alkyl, $(C_1$-$C_3)$haloalkyl or —O$(C_1$-$C_3)$alkyl;
R$_c$ is phenyl optionally substituted with one or more halo, $(C_1$-$C_3)$alkyl, $(C_1$-$C_3)$haloalkyl or —O$(C_1$-$C_3)$alkyl;
R$_d$ is phenyl optionally substituted with one or more halo, $(C_1$-$C_3)$alkyl, $(C_1$-$C_3)$haloalkyl or —O$(C_1$-$C_3)$alkyl; and
Y is a counterion;
or a pharmaceutically acceptable salt thereof, and a pharmaceutically acceptable diluent or carrier.

In certain embodiments, the anti-cancer agent is ipilimumab.

Compositions and Methods of Administration

The present invention provides a method for increasing the anticancer effects of a conventional cancer therapy (i.e., radio- and/or chemo-therapy) on cancerous cells in a mammal, comprising contacting the cancerous cell with an effective amount of PBA or a pharmaceutically acceptable salt thereof, and administering an additional conventional cancer therapy modality. In certain embodiments, the additional cancer therapy is chemotherapy and/or radiation. In certain embodiments, the PBA or a pharmaceutically acceptable salt thereof and anti-cancer agent are administered sequentially to a mammal rather than in a single composition. In certain embodiments, the mammal is a human.

In certain embodiments of the methods described above, the composition does not significantly inhibit viability of comparable non-cancerous cells.

In certain embodiments of the methods described above, the cancer is breast cancer, prostate cancer, lung cancer, pancreas cancer, head and neck cancer, ovarian cancer, brain cancer, colon cancer, hepatic cancer, skin cancer, leukemia, melanoma, endometrial cancer, neuroendocrine tumors, carcinoids, neuroblastoma, glioma, tumors arising from the neural crest, lymphoma, myeloma, or other malignancies characterized by aberrant mitochondrial hydroperoxide metabolism. In certain embodiments, the cancer is the above cancers that are not curable or not responsive to other therapies. In certain embodiments the cancer is a melanoma. In certain embodiments the cancer is a glioma.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent, is reduced by any amount between 1-100%. In certain embodiments the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

Administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Phenylbutyric acid (PBA) and the anti-cancer agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The dosage of the PBA or pharmaceutically acceptable salt thereof and the anti-cancer agent will vary depending on age, weight, and condition of the subject. Treatment may be initiated with small dosages containing less than optimal doses, and increased until a desired, or even an optimal effect under the circumstances, is reached. In general, the dosage is about 450-600 mg/kg/day in patients weighing less than 20 kg, or 9.9-13.0 g/m$^2$/day in larger patients. Higher or lower doses, however, are also contemplated and are, therefore, within the confines of this invention. A medical practitioner may prescribe a small dose and observe the effect on the subject's symptoms. Thereafter, he/she may increase the dose if suitable. In general, the PBA or pharmaceutically acceptable salt thereof and the anti-cancer agent are administered at a concentration that will afford effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include oral, parenteral, e.g., intravenous, slow infusion, intradermal, subcutaneous, oral (e.g., ingestion or inhalation), transdermal (topical), transmucosal, and rectal administration. Such compositions typically comprise the PBA or pharmaceutically acceptable salt thereof and the anti-cancer agent and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration, and a dietary food-based form. The use of such media and agents for pharmaceutically active substances is well known in the art and food as a vehicle for administration is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyethylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

"Systemic delivery," as used herein, refers to delivery of an agent or composition that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The invention will now be illustrated by the following non-limiting Examples.

Example 1

Triphenylphosphonium (TPP) compounds with linear aliphatic side chains preferentially accumulate in cancer cell mitochondria due to the hyperpolarized mitochondrial membrane potential, disturbing the cellular metabolism leading to ROS (reactive oxygen species; e.g. superoxide/hydrogen peroxide) imbalance. This perturbs the redox environment of endoplasmic reticulum (ER), consequently disturbing protein folding machinery, which results in the accumulation of mis-folded proteins and subsequent ER stress. In response to ER stress BiP (GRP78)—an ER resident molecular chaperone initiates an unregulated protein response (UPR) which works towards relieving the cell from stress. This study aims to evaluate the protective nature of ER stress in melanoma and the toxicity of TPP compounds when combined with drugs that decrease ER stress. Cell lines (A375 and SK-MEL-3) were treated with TPP derivatives in combination with 4-phenylbutyric acid (PBA), which acts as a chemical chaperone and reduces ER stress by decreasing the protein load. Our results demonstrate reducing ER stress increases the cytotoxicity of TPP derivatives in metastatic melanoma cells, thereby demonstrating the protective nature of ER stress.

Emerging evidence suggest that ER stress could play an important role in drug resistance and disease progression. Evidence reveals that decreased ER stress levels, marked by number of viable cells, ROS production levels and Cell-Surface GRP78 expression, could increase the cytotoxicity of TPP derivatives in melanoma cells when treated in combination with other drugs (e.g. PBA) overtime. Combination therapies are giving a better understanding of the protective nature of ER stress' and autophagy. A detailed understanding of the biochemical mechanism of drug resistance in melanoma can lead to a new paradigm in melanoma treatment that can improve the lives of a rapidly increasing number of metastatic melanoma patients.

Example 2

A potential combination therapy for Vemurafenib-resistant melanoma has been developed. Vemurafenib is the standard of care for advanced stage melanoma. Vemurafenib inhibits the action of $BRAF^{V600E}$ thereby resulting in programmed cell death (apoptosis). However, resistance develops rapidly to treatment with Vemurafenib.

In certain embodiments, the invention involves the use of phenyl butyric acid or a pharmaceutical salt there of (e.g., a sodium salt) in combination with vemurafenib as a treatment for metastatic melanoma. The discovery is surprising because Buphenyl® is used for a completely different disease treatment—the drug assists patients who have difficulty removing nitrogen waste. Technically, sodium phenylbutyrate is a pro-drug and is rapidly metabolized to phenylacetate. Phenylacetate is a metabolically-active compound that conjugates with glutamine via acetylation to form phenylacetylglutamine. Phenylacetylglutamine then is excreted by the kidneys. On a molar basis, it is comparable to urea (each containing two moles of nitrogen). Therefore, phenylacetylglutamine provides an alternate vehicle for waste nitrogen excretion.

In the present usage, Buphenyl® was found to reduce stress in the endoplasmic reticulum (ER). Cancer cells are generally under some stress levels above normal cells, including oxidative stress, which in turn causes basal levels of ER stress. Interestingly, the initial response (within 24 hours) of introducing Buphenyl® to melanoma cells improved their proliferation. However, somewhat fortuitously, it was discovered that when exposed to the drug for longer periods of time, vemurafenib resistant cells and cells sensitive to vemuafenib begin to die. According to the present cell survival assays, after about 6 days at levels that are similar to the plasma levels reached by tablet administration of Buphenyl®, these cells die. Further work was performed to understand the mechanism of this surprising finding and data indicated that the mechanism involved suppression of a resistance mechanism called autophagy, which can help cells to be resistant to drug treatments. Buphenyl® is normally given to patients in high doses for their entire life, which means that high dose Buphenyl® can be administered to melanoma patients in combination with vemuarfenib—potentially without new side effects.

4-phenylbutyrate (PBA) reduces ER stress by acting as a chemical molecular chaperone. The sodium salt of PBA is an FDA approved drug (BUPHENYL®), which is administered to patients suffering from urea cycle disorder. The present inventors have shown that this drug has the ability to kill vemurafenib-resistant melanoma cell lines, thus it can be potentially administered in combination with vemurafenib for the treatment of advanced stage melanoma. Studies showed that the levels of CHOP (a marker of ER stress) decreases when A375 melanoma cells are treated with a combination of vemurafenib and PBA (FIG. 6).

Experiments were also performed to determine the effect of PBA on toxicity of Vemurafenib on A375 melanoma cell lines by measuring survival fraction through mean fluorescence intensity. It was observed that as time increases the protective effect of vemurafenib decreases (6 day, vemurafenib+PBA (5 mM)) (FIG. 7). It was also observed that both the clonogenic survival and viability of vemurafenib resistant A375 melanoma cells decrease with prolonged treatment with PBA (FIG. 8).

Example 3

Studies were performed to determine the clonogenic survival in an assay using A375 cells. The cells were treated with vemurafenib, PBA and a combination of Vemurafenib, PBA and Chloroquine over a span of 6 days. 1000 cells were re-played and incubated for 14 days days. Colonies formed during this time were fixed using 70% ethanol and stained by coumassi stain. The colonies were counted and normalized to un-treated (Control) plates. Vemurafenib and PBA both individually sensitize melanoma cells. However, the combination with chloroquine is significantly more effective that either of the treatments alone (FIG. 9).

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A combination of phenylbutyric acid (PBA) or a pharmaceutically acceptable salt thereof; and an anti-cancer composition comprising two or more anti-cancer agents for the therapeutic treatment of a hyperproliferative disorder, wherein the anti-cancer agents comprise vemurafenib and hydroxychloroquine.

2. The combination of claim 1, wherein the hyperproliferative disorder is cancer.

3. The combination of claim 2, wherein the cancer is drug-resistant.

4. The combination of claim 2, wherein the cancer is melanoma.

5. The combination of claim 4, wherein the melanoma is resistant to vemurafenib treatment.

6. The combination of claim 1, wherein the PBA or the pharmaceutically acceptable salt thereof is administered simultaneously with the anti-cancer composition.

7. The combination claim 1, wherein the PBA or the pharmaceutically acceptable salt thereof and the anti-cancer composition are administered sequentially.

8. The combination of claim 1, wherein administration of the anti-cancer composition begins about 1 to about 10 days before administration of the PBA or the pharmaceutically acceptable salt thereof.

9. The combination of claim 1, wherein administration of the PBA or the pharmaceutically acceptable salt thereof begins about 1 to about 10 days before administration of the anti-cancer composition.

10. The combination of claim 1, wherein administration of the PBA or the pharmaceutically acceptable salt thereof and administration of the anti-cancer composition begin on the same day.

11. A kit comprising PBA or the pharmaceutically acceptable salt thereof, a container, and a package insert or label indicating the administration of the PBA or the pharmaceutically acceptable salt thereof with two or more anti-cancer agents for treating a hyperproliferative disorder, wherein the anti-cancer agents comprise vemurafenib and hydroxychloroquine.

12. A method for treating a hyperproliferative disorder in a mammal, comprising administering to the mammal a combination of PBA or the pharmaceutically acceptable salt thereof; and vemurafenib and hydroxychloroquine.

13. The method of claim 12, wherein the PBA or pharmaceutically acceptable salt thereof is administered for more than a month.

14. The method of claim 12, wherein the PBA or pharmaceutically acceptable salt thereof is administered for more than a year.

15. The method of claim 12, wherein the PBA or pharmaceutically acceptable salt thereof is administered at a dosage of at least 1500 mg/day.

* * * * *